US008679310B2

(12) United States Patent
Murase et al.

(10) Patent No.: US 8,679,310 B2
(45) Date of Patent: Mar. 25, 2014

(54) BIOSENSOR

(75) Inventors: Yosuke Murase, Kyoto (JP); Koji Katsuki, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 280 days.

(21) Appl. No.: 13/091,325

(22) Filed: Apr. 21, 2011

(65) Prior Publication Data

US 2011/0259741 A1 Oct. 27, 2011

(30) Foreign Application Priority Data

Apr. 22, 2010 (JP) .................................. 2010-098416
Apr. 6, 2011 (JP) .................................. 2011-084225

(51) Int. Cl.
*G01N 27/327* (2006.01)

(52) U.S. Cl.
USPC ................................ 204/403.04; 204/403.11

(58) Field of Classification Search
USPC ............. 204/403.01–403.15; 205/777.5, 778, 205/792
See application file for complete search history.

(56) References Cited

U.S. PATENT DOCUMENTS

| 5,120,420 | A | * | 6/1992 | Nankai et al. ............. 204/403.11 |
| 5,356,786 | A | | 10/1994 | Heller et al. ..................... 435/14 |
| 5,672,256 | A | * | 9/1997 | Yee ............................. 422/82.01 |
| 6,083,710 | A | * | 7/2000 | Heller et al. ................... 600/347 |
| 7,003,341 | B2 | | 2/2006 | Say et al. ........................ 600/345 |
| 7,190,988 | B2 | | 3/2007 | Say et al. ........................ 600/345 |
| 7,366,556 | B2 | | 4/2008 | Brister et al. .................. 600/347 |
| 7,424,318 | B2 | | 9/2008 | Brister et al. .................. 600/347 |
| 7,460,898 | B2 | | 12/2008 | Brister et al. .................. 600/347 |
| 7,462,264 | B2 | | 12/2008 | Heller et al. ............. 204/403.11 |
| 7,467,003 | B2 | | 12/2008 | Brister et al. .................. 600/347 |
| 7,732,179 | B2 | * | 6/2010 | Boenitz-Dulat et al. ...... 435/190 |
| 2005/0139489 | A1 | * | 6/2005 | Davies et al. .................... 205/775 |
| 2007/0105173 | A1 | | 5/2007 | Takeshima et al. |
| 2007/0131549 | A1 | * | 6/2007 | Cai et al. .................. 204/403.02 |
| 2008/0197024 | A1 | * | 8/2008 | Simpson et al. ............. 205/778 |
| 2011/0139617 | A1 | * | 6/2011 | Fransaer et al. ......... 204/403.14 |

FOREIGN PATENT DOCUMENTS

JP 08-327587 A * 12/1996 ........... G01N 27/414

OTHER PUBLICATIONS

JPO computer-generated English language translation of the Claims and Description of Kajiwara JP 08-327587 A, downloaded Mar. 18, 2013.*
Poriton of BRENDA tabulated Turnover numbers for EC 1.1.5.2-quinoprotein glucose dehydrogenase including D-glucose as substrate downloaded on Mar. 19, 2013 from http://www.brenda-enzymes.org/php/result_flat.php4?ecno=1.1.5.2&UniProtAcc=P15877&OrganismID=2026&ShowAll=True.*
Poriton of BRENDA tabulated Turnover numbers for EC 1.1.3.4-glucose oxidase including D-glucose and beta-D-glucose as substrates downloaded on Mar. 19, 2013 from http://www.brenda-enzymes.info/php/result_flat.php4?ecno=1.1.3.4.*
Office Action dated Dec. 5, 2013 in corresponding German Patent Application No. 102011007918.1 with English language translation Summary.

* cited by examiner

*Primary Examiner* — Alex Noguerola
(74) *Attorney, Agent, or Firm* — Morgan, Lewis & Bockius LLP

(57) ABSTRACT

A biosensor includes a first working electrode that a biocatalyst, which has a property that reacts on a specified ground substance, is disposed, a second working electrode that the biocatalyst, which the property is lost, is disposed, and at least one counter electrode for respectively applying a voltage to the first working electrode and the second working electrode.

6 Claims, 13 Drawing Sheets

BIOSENSOR

This application claims the benefit of Japanese Patent Application No. 2010-098416 filed on Apr. 22, 2010 and Japanese Patent Application No. 2011-084225 filed on Apr. 6, 2011 in the Japanese Patent Office, the disclosure of each of which is herein incorporated in its entirety by reference.

BACKGROUND OF THE INVENTION

The present invention relates to a biosensor which measures a specified ground substance contained in a body fluid of a human being and an animal.

A conventional known technology is a technology of measuring the numerical value information on the subject substance in the body fluid such as a blood, urine and an interstitial liquid, e.g., measuring continuously a glucose concentration (which is a so-called a blood glucose level) in an interstitial liquid of the examinee by employing an electrochemical sensor embedded in an abdomen or an arm of the examinee. The electrochemical sensor is a sensor capable of detecting a minute amount of electric current by making use of electrochemical reaction, and is suited to detecting a minute amount of chemical substance in which oxidation-reduction reaction occurs.

The electrochemical sensor for measuring the glucose concentration may involve using, in many cases, a biosensor which detects a subject substance in a sample by utilizing enzyme reaction in a way that immobilizes the enzyme to a sensor portion. This type of biosensor generally has a working electrode and a counter electrode, in which the enzyme (e.g., glucose oxidase) is immobilized on the working electrode. The glucose concentration may be measured based on a response current obtained when applying a voltage to between the working electrode and the counter electrode.

The glucose oxidase produces gluconic acid by selectively reacting on the glucose under an existence of oxygen. Then, the oxygen is reduced, while hydrogen peroxide proportional to a quantity of the glucose is generated. The hydrogen peroxide can be oxidized electrochemically easily and can be therefore measured by use of a pair of electrodes. Namely, the response current value can be obtained by electrical oxidizing the hydrogen peroxide generated by the enzyme reaction of the enzyme. Then, the glucose concentration can be calculated based on a sampling current obtained by periodically sampling the electric current from the response current values acquired continuously.

By the way, a living body fluid contains an interference substance that affects a measurement value of the response current for measuring the glucose described above as the case may be. Known interference substances are exemplified by ascorbic acid, erythrocyte and vitamin C. If the interference substance is contained in the living body fluid serving as a measurement target fluid of a glucose concentration, the response current includes a signal component derived from nonenzymatic reaction (nonspecific reaction) like reaction between the interference substance and the electrode and a signal component derived from the oxidation-reduction reaction based on the enzyme. In this case, it has possibility that the glucose concentration acquired based on the response current is remarkably different from an actual value.

In an observation of the response current, it is difficult to determine whether the response current contains the signal component derived from the nonspecific reaction or not. Such being the case, there is a conventional technology (e.g., Patent document 1) of forming an interference-substance removing film on an electrode of a sensor and preventing interference substances other than a biometric component from reacting on the electrode.

[Patent document 1] U.S. Pat. No. 5,356,786
[Patent document 2] U.S. Pat. No. 7,003,341
[Patent document 3] U.S. Pat. No. 7,190,988
[Patent document 4] U.S. Pat. No. 7,462,264

The technology of forming the interference substance removing film disclosed in Patent document 1 has, however, a complicated configuration to dispose a reagent on the electrode. Further, the interference substance removing film can remove only an intended specified interference substance.

SUMMARY OF THE INVENTION

It is an object of the present invention, which was devised in view of the circumstances described above, to provide a technology capable of restraining affection of an interference substance and obtaining a result of measuring a physical quantity of a ground substance with high accuracy.

The present invention adopts configurations below in order to solve the above-mentioned problems. A first aspect of the present invention is a biosensor. The biosensor includes: a first working electrode that a biocatalyst, which has a property that reacts on a specified ground substance, is disposed; a second working electrode that the biocatalyst, which the property is lost, is disposed; and at least one counter electrode for respectively applying a voltage to the first working electrode and the second working electrode.

According to the first aspect of the present invention, when applying the voltage to between at least one counter electrode and the first working electrode and between the at least one counter electrode and the second working electrode, a response current (which is termed a first response current) from the first working electrode and a response current (which is termed a second response current) from the second working electrode are obtained. The first response current contains a signal component deriving from reaction (biocatalyst reaction) between the biocatalyst and the specified ground substance and a signal component not deriving from the biocatalyst reaction, while the second response current does not contain the signal component derived from the reaction between the biocatalyst and the specified ground substance. Namely, it is presumable that the second response current includes only the signal component not deriving from the biocatalyst reaction. Hence, for instance, the signal component deriving from the biocatalyst reaction may be extracted from the first response current by subtracting the second response current from the first response current. Thus, it is possible to obtain a precise physical quantity (e.g., a concentration) of the specified ground substance.

In the first aspect, the number of the counter electrode for obtaining the response currents respectively from the first working electrode and the second working electrode is not limited to one. Namely, the counter electrodes corresponding respectively to the first working electrode and the second working electrode may be prepared. As a matter of course, it is feasible to reduce the number of steps for manufacturing the biosensor and to downsize and simplify the biosensor by providing one single counter electrode common to the first and second working electrodes. Further, a reference electrode other than the counter electrode and the working electrodes may also be provided.

The first aspect of the present invention may be adopted a configuration that the biocatalyst having the property reacting on the specified ground substance is disposed on the second working electrode, and the property of the biocatalyst is deactivated by providing energy to the second working electrode. For example, at least one of thermal energy and electric energy may be employed as the energy.

The first aspect of the present invention may be adopted a configuration that the biocatalyst having the property reacting on the specified ground substance is disposed on the second working electrode, and a material for making the biocatalyst lose, the property or for inhibiting the property is added.

Moreover, the biocatalyst applicable to the present invention is, for example, an enzyme. What is selected as the enzyme is an enzyme corresponding to the specified ground substance defined as a physical quantity measuring target substance. For example, if the specified ground substance is glucose, glucose oxidase (GOD) and glucose dehydrogenase (GDH) may be applied as the enzymes.

The second aspect of the present invention is a biosensor including: a first working electrode that a first biocatalyst, which has a property that reacts on a specified ground substance, is disposed; a second working electrode that a second biocatalyst, which has the property, is disposed; and at least one counter electrode for respectively applying a voltage to the first working electrode and the second working electrode, wherein a reaction speed of the first biocatalyst with the ground substance is different from a reaction speed of the second biocatalyst with the ground substance.

According to the second aspect of the present invention, the reaction speeds of the first biocatalyst and the second biocatalyst with respect to the ground substance are different from each other. To be specific, each of the first biocatalyst and the second biocatalyst has at least one of a different maximum speed Vmax and a different Michaelis constant Km. In other words, these two biocatalysts have calibration curves different from each other. This implies that the calibration curve for obtaining the physical quantity of the ground substance from the reaction on the first biocatalyst, is different from the calibration curve for obtaining the physical quantity of the ground substance from the reaction on the second biocatalyst.

Then, the biosensor according to the second aspect obtains, with respect to the same body fluid, a response current y from the first working electrode and a response current y' from the second working electrode, in which case the response currents y and y' may be expressed as below on the assumption that the interference substance contained in the body fluid equally affects the first working electrode and the second working electrode.

$$y = ax + c \quad (1)$$

$$y' = bx + c \quad (2)$$

Herein, c is a signal component derived from, the reaction of a non-biocatalyst such as the interference substance, a is a calibration curve coefficient corresponding to the first biocatalyst, and b is a calibration curve coefficient corresponding to the second biocatalyst. Further, x is a physical quantity of the specified ground substance in the body fluid. The following formula (3) for obtaining the physical quantity x can be acquired by use of the formulae (1) and (2).

$$x = (y - y')/(a - b) \quad (3)$$

It is therefore feasible to accurately measure the physical quantity of the specified ground substance.

The first and second biocatalysts in the second aspect are, for example, an enzyme. The enzymes explained regarding the first aspect are applicable. Further, an enzyme obtained by genetic modification of the first biocatalyst is applicable as the second biocatalyst.

The third aspect of the present invention is a biosensor including: a first working electrode that a first biocatalyst, which has a property that reacts on a specified, ground substance, is disposed; a second working electrode that a second biocatalyst, which has the property, is disposed; and at least one counter electrode for respectively applying a voltage to the first working electrode and the second working electrode, wherein a reaction area on the first working electrode is different from a reaction area on the second working electrode.

According to a third aspect of the present invention, the reaction areas on the first working electrode and the second working electrode are different from each other, and, similarly to the second aspect, it follows that the calibration curve for obtaining the physical quantity of the specified ground substance from the response current coming from the first working electrode, is different from the calibration curve for obtaining the physical quantity of the specified ground substance from the response current coming from the second working electrode. Hence, the physical quantity x of the specified ground substance can be obtained by the same technique as in the second embodiment, thereby enabling the precise physical quantity x to be measured.

The fourth aspect of the present invention is a biosensor including: a first working electrode that a first biocatalyst, which has a property that reacts on a specified ground substance, is disposed; a second working electrode that a second biocatalyst, which has the property, is disposed; and at least one counter electrode for respectively applying a voltage to the first working electrode and the second working electrode, wherein a total reaction activity on the first working electrode is different from a total reaction activity on the second biocatalyst.

According to a fourth aspect of the present invention, the respective total reaction activities on the first working electrode and the second working electrode are different from each other, whereby similarly to the second and third mode the calibration curve for obtaining the physical quantity of the specified ground substance from the response current coming from the first working electrode, is different from the calibration curve for obtaining the physical quantity of the specified ground substance from the response current coming from the second working electrode. Therefore, the physical quantity x of the specified ground substance can be obtained by the same technique as in the second embodiment, thereby enabling the precise physical quantity x to be measured.

The first biocatalyst and the second biocatalyst in the third and fourth aspects may also be the same type of biocatalysts and may also be different biocatalysts. Moreover, each of the first biocatalyst and the second biocatalyst is, e.g., an enzyme, and the enzyme explained in the first aspect, may be applied.

The fifth aspect of the present invention is a monitoring apparatus including: a first detection unit which detects a first signal value from a first working electrode obtained by applying a voltage to between the first working electrode and a counter electrode, wherein a biocatalyst having a property reacting on a specified ground substance is disposed oh the first working electrode; a second detection unit which detects a second signal value from a second working electrode obtained by applying a voltage to between the second working electrode and the counter electrode, wherein the biocatalyst that the property is lost is disposed on the second working electrode; a correction unit which corrects a concentration of the specified ground substance that is calculated from the first signal value by the second signal value; and an output unit which outputs the corrected concentration of the specified ground substance.

In the fifth aspect, the correction unit may calculate a value obtained by subtracting the second signal value from the first signal value as the corrected concentration of the specified ground substance.

The sixth aspect of the present invention is a monitoring apparatus including: a first detection unit which detects a first signal value from a first working electrode obtained by applying a voltage to between the first working electrode and a counter electrode, wherein a first biocatalyst having a property reacting on a specified ground substance is disposed on the first working electrode; a second detection unit which detects a second signal value from a second working electrode obtained by applying a voltage to between the second working electrode and the counter electrode, wherein a second biocatalyst having the property and a reaction speed differing from the first biocatalyst is disposed on the second working electrode; a correction unit which corrects a concentration of the specified ground substance that is calculated from the first signal value by the second signal value; and an output unit which outputs the corrected concentration of the specified ground substance.

In the sixth aspect, the correction unit obtains a concentration x(t) of the specified ground substance based on a following formula, wherein the formula is used under a premise that: the first signal value y(t) at a certain point of time t is expressed by a linear function y(t)=ax(t)+c, where a is a calibration curve coefficient corresponding to the first biocatalyst, x is a concentration of the specified ground substance and c is a signal component based on a substance excluding the specified ground substance in a body fluid; the second signal y'(t) at the certain, point of time t is expressed by a linear function y'(t)=bx(t)+c, where b is a calibration curve coefficient corresponding to the second biocatalyst, x is the concentration of the specified ground substance and c is the signal component; and a value of the signal component c in the first signal value y(t) is equal to a value of the signal component c of the second signal value y'(t).

$$x(t)=(y(t)-y'(t))/(a-b) \quad \text{(Formula)}$$

The seventh aspect of the present invention is a non-transitory computer readable medium recording a program executed by an information processing apparatus to perform: detecting a first signal value from a first working electrode obtained by applying a voltage to between the first working electrode and a counter electrode, wherein a biocatalyst having a property reacting on a specified ground substance is disposed on the first working electrode; detecting a second signal value from a second working electrode obtained by applying a voltage to between the second working electrode and the counter electrode, wherein the biocatalyst that the property is lost is disposed on the second working electrode; correcting a concentration of the specified ground substance that is calculated from the first signal value by the second signal value; and outputting the corrected concentration of the specified ground substance.

The seventh aspect may adopt a configuration that, as the corrected concentration of the specified ground substance, a value obtained by subtracting the second signal value from the first signal value may be calculated in the correcting step.

The eighth aspect of the present invention is a non-transitory computer readable, medium recording a program executed by an information processing apparatus to perform: detecting a first signal value from a first working electrode obtained by applying a voltage to between the first working electrode and a counter electrode, wherein a first biocatalyst having a property reacting on a specified ground substance is disposed on the first working electrode; detecting a second signal value from a second working electrode obtained by applying a voltage to between the second working electrode and the counter electrode, wherein a second biocatalyst having the property and a reaction speed differing from the first biocatalyst is disposed on the second working electrode; correcting a concentration of the specified ground substance that is calculated from the first signal value by the second signal value; and outputting the corrected concentration of the specified ground substance.

The eighth aspect may adopt a configuration that a concentration x(t) of the specified-ground substance is obtained based, on a following formula, wherein the formula is used under a premise that: the first signal, value y(t) at a certain point of time t is expressed by a linear function y(t)=ax(t)+c, where a is a calibration curve coefficient corresponding to the first biocatalyst, x is a concentration of the specified ground substance and c is a signal component based on a substance excluding the specified ground substance in a body fluid; the second signal, y'(t) at the certain point of time t is expressed by a linear function y'(t)=bx(t)+c, where b is a calibration curve coefficient corresponding to the second biocatalyst, x is the concentration of the specified ground substance and c is the signal component; and a value of the signal component c in the first signal value y(t) is equal to a value of the signal component c of the second signal, value y'(t).

$$x(t)=(y(t)-y'(t))/(a-b) \quad \text{(Formula)}$$

Furthermore, the present invention may be specified as the invention of a measuring method having substantially the same configuration as those in the seventh and eighth aspects.

According to the aspects of the present invention, it is feasible to acquire the result of measuring the physical quantity of the ground substance with the high accuracy, which restrains the affection of the interference substance.

BRIEF DESCRIPTION OF THE DRAWINGS

FIG. 2(A) is a plan view; and FIG. 2(B) is a sectional view taken along the line A-A.

DETAILED DESCRIPTION OF THE INVENTION

Embodiments of the present invention will hereinafter be described with reference to the drawings. Configurations in the embodiments are exemplifications, and the present invention is not limited to the configurations in the embodiments.

[First Embodiment]

Figure 1:
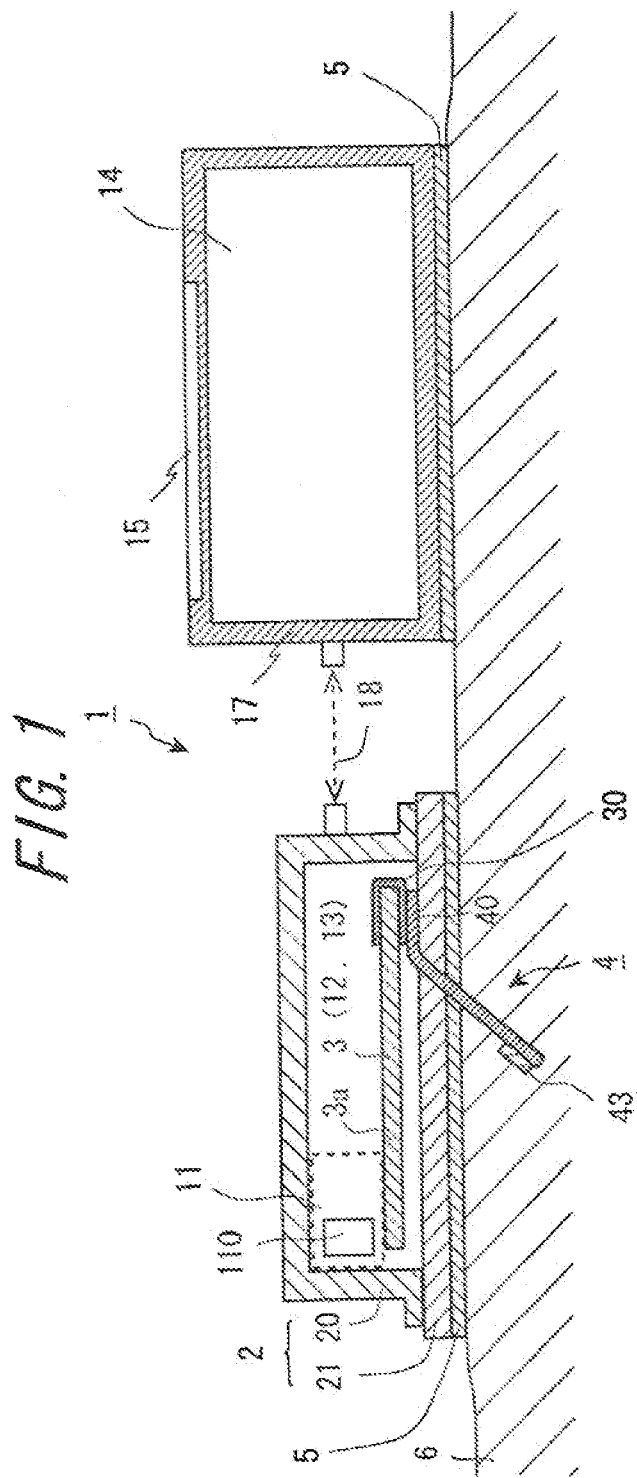
FIG. 1 is a diagram illustrating an outline of a configuration of a monitoring apparatus in a first embodiment of the present invention.

FIG. 1 is a view illustrating an outline of a configuration of a monitoring device (monitoring apparatus) 1 according to a first embodiment. A monitoring apparatus 1 depicted in FIG. 1 is used for automatically continuously measuring a glucose concentration in a blood or an interstitial liquid of the human being or ah animal as a physical quantity of a specified ground substance in a body fluid. The monitoring apparatus 1 includes a housing 2, a control computer 3 and an electrochemical sensor 4.

The electrochemical sensor 4 is a sensor which detects a specified subject substance by making use of electrochemical reaction. A biosensor is applied in the embodiments. The biosensor uses a living organism or a material derived from the living organism as an element for detecting the subject substance in order to continuously measure and detect the subject substance.

The electrochemical sensor 4 in the embodiments is employed for continuously measuring the glucose concentration in ah interstitial liquid or blood. The electrochemical sensor (biosensor) 4 will therefore be referred to as a "glucose sensor 4".

The housing 2 takes an, external shape of the monitoring apparatus 1 and includes a cover 20 and a base plate 21. The cover 20 and the base plate 21, which are fixed to each other, define the housing 2 accommodating the control computer 3. The housing 2 is made from materials having a waterproofing property and/or a water resisting property. In the housing 2, e.g., at least the cover 20 (and the base plate 21 as the necessity may arise) may be composed of materials having low permeability, such as metals and/or synthetic resins. An applicable material as the synthetic resin is, for example, polypropylene.

An one end portion 40A of the glucose sensor 4 is fixed to the base plate 21, and another end portion 40B of the glucose sensor 4 extends outside the housing 2 via an opening (unillustrated) formed in the base plate 21. A bonding film 5 is fixed to an external surface of the base plate 21. The bonding film 5 is used for fixing the monitoring apparatus 1 onto the skin of the examinee. For example, a double-sided tape having adhesions on both faces may be employed as the bonding film 5.

The control computer 3 includes electronic components including a computer required for performing predetermined operations, for measuring the glucose such as applying a voltage to the glucose sensor 4 and computing the glucose concentration from a response current, and includes a terminal 30 for establishing an electrical contact with an electrode 42 of the glucose sensor 4. The terminal 30 is employed for acquiring a response current value from the glucose sensor 4 by applying the voltage to the glucose sensor 4.

The glucose sensor 4 is used for acquiring the response corresponding to the glucose concentration in the interstitial liquid. The other end portion 40B of the glucose sensor 4 is provided with a sensor portion to which an enzyme being a biocatalyst for detecting the glucose in the interstitial liquid is immobilized, and the sensor portion is employed in the way of being at least implanted subcutaneously. An example of the first embodiment is that a portion of the glucose sensor 4, which protrudes outside as depicted in FIG. 1 from the base plate 21 of the housing 2, is inserted into a skin 6.

Figure 2:
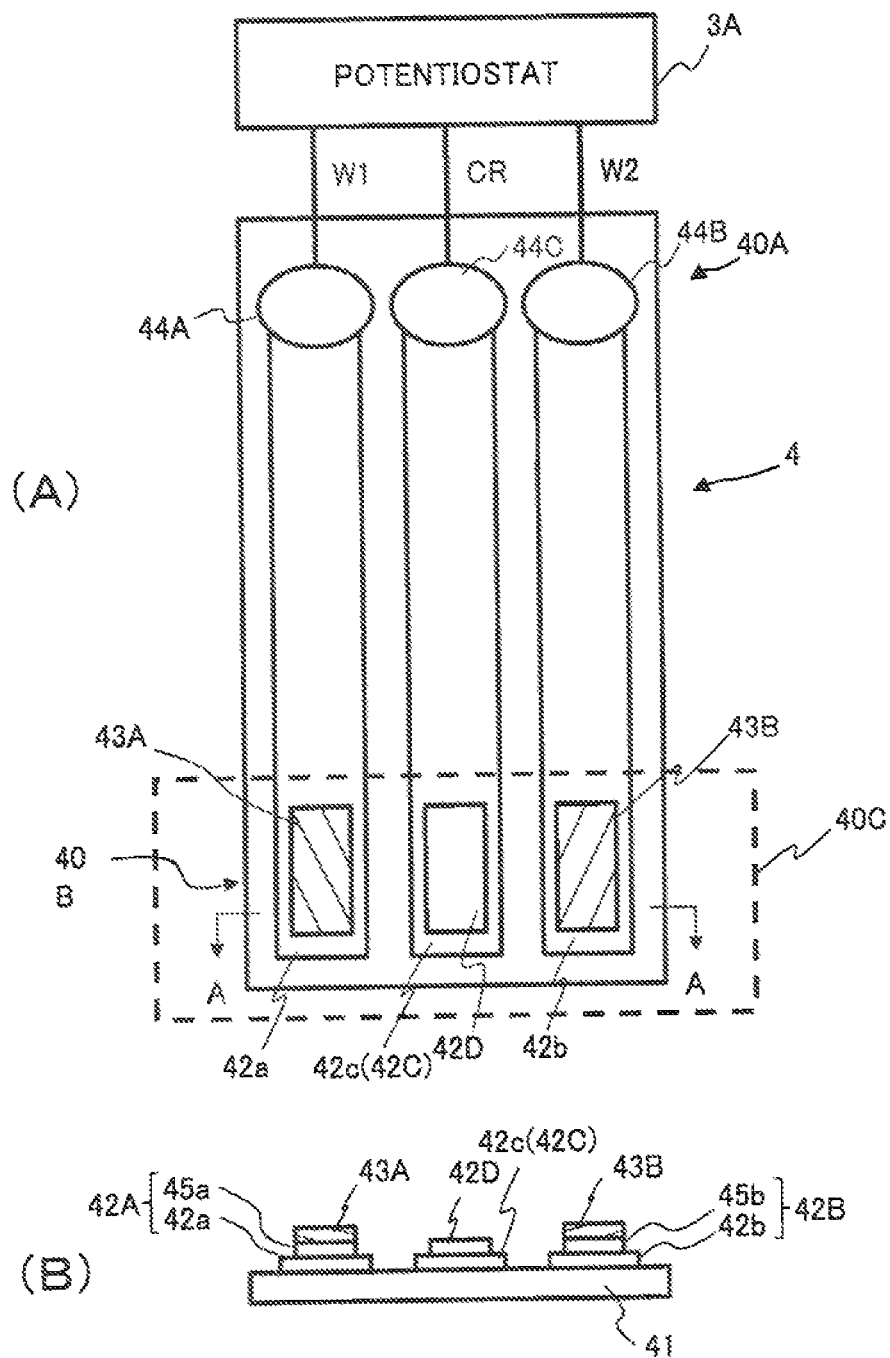
FIG. 2 is a view illustrating an example of a configuration of a biosensor (glucose sensor) depicted in FIG. 1.

FIG. 2 is a diagram illustrating an example of a configuration of the glucose sensor 4 according to the first embodiment of the present invention; FIG. 2(A) is a plan view of the glucose sensor 4; and FIG. 2(B) is a sectional view, taken along the line A-A, of the glucose sensor depicted in FIG. 2(A). As illustrated in FIGS. 2(A) and 2(B), the glucose sensor 4 includes a base plate 41, an electrode and a lead wire that are formed on the base plate 41, and an enzyme-immobilized portion.

To be specific, metal layers 42a, 42b and 42c are formed on one surface of the base plate 41. The metal layers. 42a, 42b and 42c are grown on one single surface of the film-shaped base plate 41 by physical-vaport depositing (PVD, e.g., sputtering) or by chemical-vapor-depositing (CVD) a metal such as gold and platinum on the one surface and performing laser-based trimming. Applicable materials for the base plate 41 are thermoplastic resins such as polyethyleneterephthalate (PET), polypropylene (PP) and polyethylene (PE) and resins such as a polyimide resin and an epoxy resin not having any harmful effect in the human body but having a proper insulating property and flexibility.

Each of the metal layers 42a, 42b and 42c is formed in a longitudinal direction of the base plate 41 and extends from an one end to another end of the base plate 41. The other end of each of the metal layers 42a, 42b and 42c. are utilized as a first working electrode 42A, a second working electrode 42B and a counter electrode 42C. By contrast, intermediate portions and the one ends of the metal layers 42a, 42b and 42c are respectively utilized as lead wires.

The one ends of the metal layers 42a, 42b and 42c are individually connected to contact pads 44A, 44B, 44C provided at the one end of the base plate 41. The contact pads 44A, 44B, 44C are utilized for an electrical connection with the terminal 30 (FIG. 1) of the control computer 3. The contact, pads 44A, 44B, 44C may be formed integrally with the electrodes and the lead wire by trimming the metal layers 42a, 42b, 42c. The contact pads 44A, 44B, 44C may also be formed by employing, as a matter of course, a conductor in a process differing from a forming process of the metal layers. In the first embodiment, the terminal 30 includes terminals W1, W2 and a terminal CR of a potentiostat 3A connected to the control computer 3, and the contact pads 44A, 44B, 44C are connected to the terminals W1, W2, CR, respectively.

Specifically, in FIG. 1, though the illustrations of the contact pads 44A, 44B, 44C are omitted, the base plate 41 of the monitoring apparatus 1 is joined to the cover 20, in which case such a state occurs that the one end of the glucose sensor 4 is sandwiched between a substrate 3a of the control computer 3 and the base plate 21 to fix the glucose sensor 4. Then, the terminal 30 provided at the substrate 3a is fixed in a state of being pressed by the contact pads 44A, 44B, 44C, whereby the glucose sensor 4 and the monitoring apparatus 1 come to a state of being electrically connected to each other.

A reference electrode 42D is formed on a predetermined area of the metal layer 42c as the counter electrode 42C. The reference electrode 42D may be formed by coating or printing, e.g., a silver-silver chloride ink over the predetermined area on the counter electrode 42C.

On the other hand, carbon layers 45a, 45b formed by screen-printing a carbon paste are stacked on the predetermined area on the another-end sides of the metal layers 42a, 42b. Thus, the first working electrode 42A including the metal layer 42a and the carbon layer 45a is formed, and the second working electrode 42B including the metal layer 42b and the carbon layer 45b is formed.

As described above, the glucose sensor 4 in the embodiments includes the electrode 42 constructed of the first working electrode 42A, the second working electrode 42B, the counter electrode 42C and the reference electrode 42D. The reference electrode 42D may be, however, omitted. Further, though providing the counter electrode 42C common to the first working electrode 42A and the second working electrode 42B in the example illustrated in FIG. 2, two counter electrodes corresponding respectively to the first working electrode 42A and the second working electrode 42B may also be provided.

Enzyme-immobilized layers 43A, 43B, to which the enzyme is immobilized, are formed on the carbon layers 45a, 45b, respectively. The enzyme-immobilized layers 43A, 43b are formed in a way that dispenses glucose dehydrogenase (GDH) reacting on the glucose over the carbon layers 45a, 45b and immobilizes GDH with an immobilizing substance such as glutaraldehyde. In the manner described above, the sensor portion 40C is configured at the other end portion of the glucose sensor 4. Hereinafter, the enzyme-immobilized layer 43A will be termed a first enzyme-immobilized portion 43A, and the enzyme-immobilized layer 43b will be termed a second enzyme-immobilized portion 43b as the case may be.

The first working electrode 42A and the second working electrode 42B are disposed with the counter electrode 42C being sandwiched in therebetween, in which the first working electrode 42A, the second working electrode 42B and the counter electrode 42C are arranged at distances equal to each other. Moreover, the carbon layers 45a, 45b and the enzyme-immobilized layers 43A, 43B are formed to equalize square measures (areas) thereof, and the enzyme-immobilized layers 43A, 43B are also constructed to equalize quantities of enzymes contained therein. Namely, the glucose sensor 4 includes the two working electrodes 42A and 42B having the same configuration and the first and second enzyme-immobilized portions 43A, 43B (the enzyme-immobilized portion 43 in FIG. 1).

Figure 3:
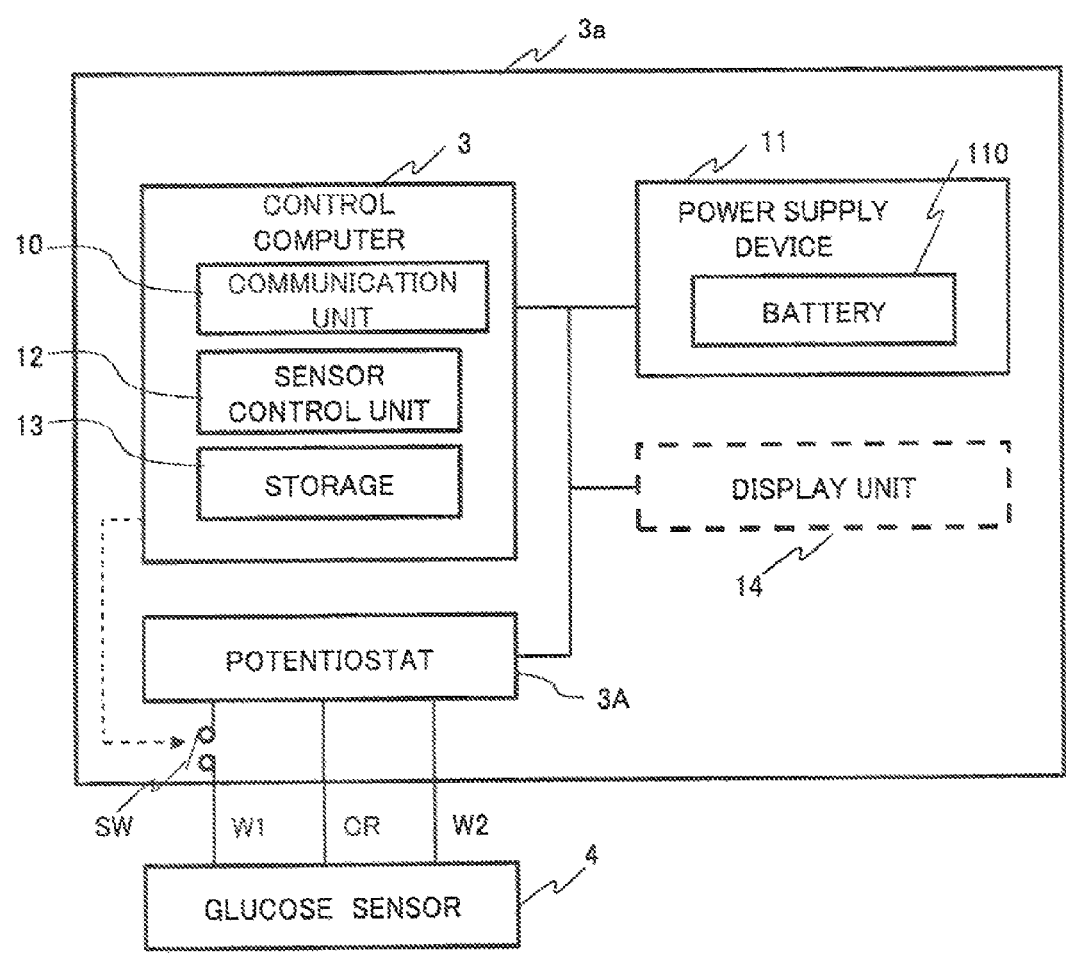
FIG. 3 is a diagram showing an example of a configuration related to a control computer depicted in FIG. 1.

FIG. 3 illustrates an example of main electronic components accommodated within the monitoring apparatus 1. As depicted in FIG. 3, the housing 2 accommodates the substrate 3a provided with the control computer 3, the potentiostat 3A and a power supply device 11. A display unit 14, though illustrated in the way of being embraced by the substrate 3a in FIG. 3, actually has, as depicted in FIG. 1, a display panel 15 for displaying a computed result of the glucose concentration.

Further, a housing 17 of the display unit 14 may be fixed onto the skin via the bonding film 5 in the same way as the housing 2 may be.

Referring back to FIG. 3, the control computer 3 includes hardwarewise a processor such as a CPU (Central Processing Unit), a recording medium such as a memory (RAM (Random Access Memory)) and a ROM (Read Only Memory), a communication unit and an unillustrated Input/Output (I/O) device. The control computer 3 functions as a device including a communication unit 10, a control unit 12 and a storage 13 in such a manner that the processor loads the program stored on the recording medium (e.g., the ROM) into the RAM and then executes the program. Note that the control computer 3 may also include an auxiliary storage device such as a semiconductor memory (EEPROM (Electrically Erasable Programmable ROM, a flash memory) and a hard disc.

The control unit 12 controls a voltage application timing, an applied voltage value, sampling of the response current, the computation of the glucose concentration or communications with external information processing terminals. The communication unit 10 performs data communications with the display unit 14 (FIG. 1), and transmits the computed result of the glucose concentration given by the control unit 12 to the display unit 14. Communications available as the data communications are wired communications using a cable, and wireless communications (IrDA, Bluetooth) utilizing infrared-rays and radio transmission may be also applied. The display unit 14 is capable of displaying, for example, the computed result of the glucose concentration received from the monitoring apparatus 1. in a predetermined format on the display screen (the display panel 15).

The power supply device 11 has a battery 110, and supplies electric power for operation to the control computer 3 and the potentiostat 3A. Note that the power supply device 11 may be also placed outside the housing 2.

The potentiostat 3A is defined as a device which makes electric potentials of the first working electrode 42A and the second working electrode 42B constant to the reference electrode 42D. The potentiostat 3A, via the terminals CR, W1 and W2, applies a predetermined voltage to between the counter electrode 42C and the first working electrode 42A and between the counter electrode 42G and the second working electrode 42B, then measures a response current (a second response current) of the second working electrode 42B that is acquired at the terminal W2 as well as measuring a response current (a first response current) of the first working electrode 42A that is acquired at the terminal W1, and transmits measured results of the first and second response currents to the control unit 12.

It is to be noted that the display unit 14 may incorporate the functions as the control unit 12 and the storage unit 13, while on the side of the housing 2 the communication unit 10 may transmit the measured results of the potentiostat 3A to the display unit 14. Alternatively, the control computer 3 and the potentiostat 3A may become on-board devices of the display unit 14, whereby the potentiostat 3A mounted on the display unit 14 may execute applying the voltage to the glucose sensor 4 and detecting the response current therefrom.

Figure 4:
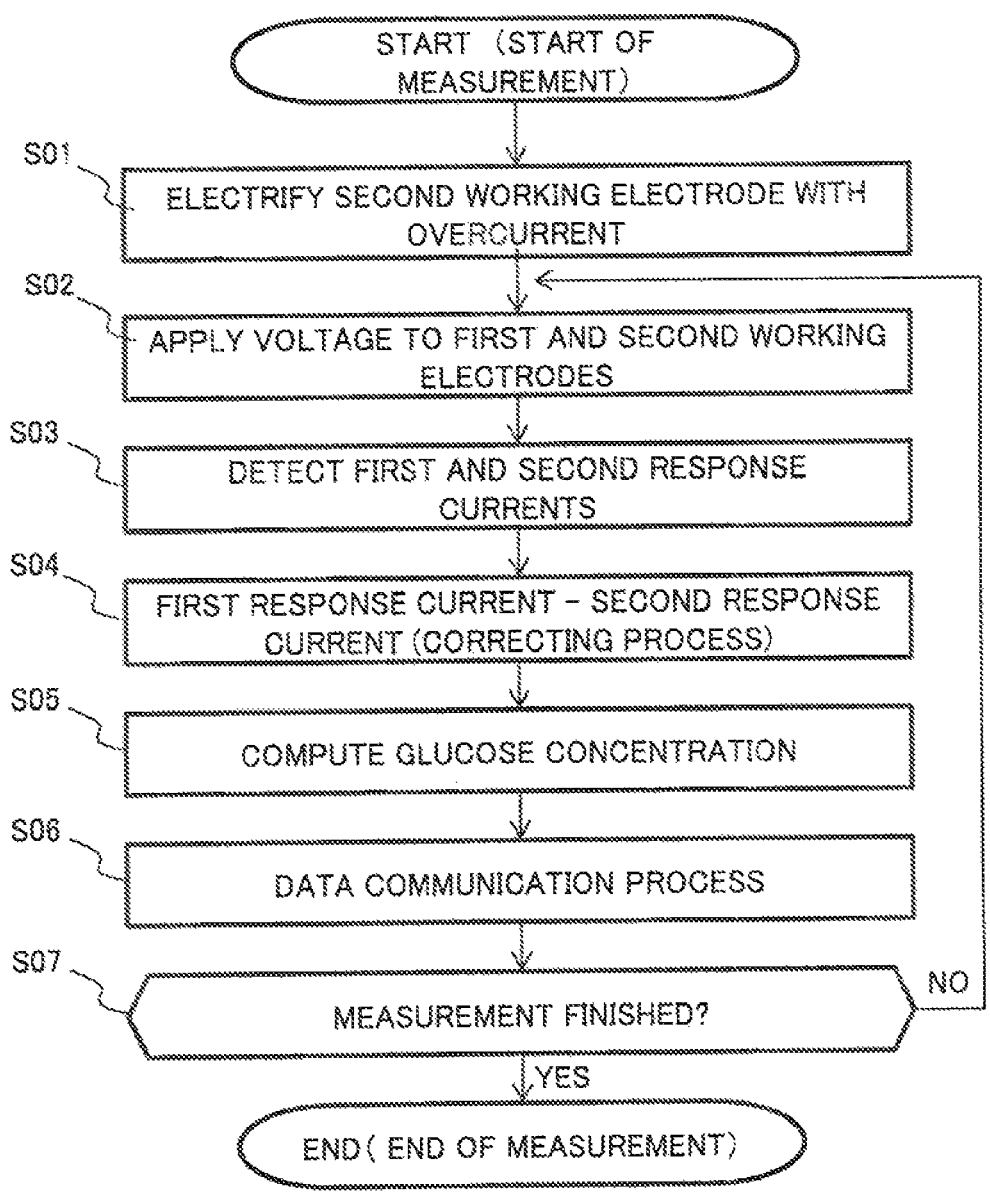
FIG. 4 is a flowchart showing an example of program processing of a control unit according to the first embodiment.

FIG. 4 is a flowchart illustrating an example of a glucose concentration measuring process of the control computer 3 in the first embodiment. A premise is that the monitoring apparatus 1 and the glucose sensor 4 are properly set in predetermined locations (an abdomen or an arm) of an examinee, and the sensor unit 40C is immersed in the interstitial liquid.

In FIG. 4, the CPU (the control unit 12) of the control computer 3, when accepting a glucose concentration measurement start instruction issued from the outside, controls the potentiostat 3A to electrify only the second working electrode 42B with an overcurrent (Step S01). The monitoring apparatus 1, which has an unillustrated input device, may input measurement start/end instructions to the control computer 3 by use of the input device. The control unit 12 accepting the start instruction, for example, releases a switch SW provided between the first working electrode 42A and the terminal W1 to set a status of the current not flowing to the first working electrode 42A. On the other hand, the control unit 12 provides the overcurrent through between the counter electrode 42C and the first working electrode 42A for a predetermined period of time. Thereby, the enzyme (GDH) immobilized to the second enzyme-immobilized portion 43B on the second working electrode 42B is set in a deactivated state. The overcurrent is to be a current having such a level as to damage neither the counter electrode 42C nor the second working electrode 42B through the electrification. A current value to be electrified and electrification time may be properly set in consideration from an amount of the enzyme and a deactivation speed of the enzyme.

By the electrification of the overcurrent to the second working electrode 42B, the second working electrode 42B comes to a status having the same configuration as on the side of the first working electrode 42A except the status of losing a property that the enzyme reacts oh the glucose defined as a specified ground substance.

Next, the control unit 12 closes the switch SW, controls the potentiostat 3A, then starts applying the predetermined voltage to the first working electrode 42A and the second working electrode 42B (Step S02), and starts measuring the response current (the first response, current) from the first working electrode 42A and the response current (the second response Current) from the second working electrode 42B (Step S03). The potentiostat 3A measures respectively the first and second response currents acquired by applying the voltage, and transmits the measured results to the control unit 12.

The control unit 12 executes a correcting process of correcting the first response current by use of the second response current (Step S04). Namely, the control unit 12 executes the following processes. Herein, the first response current value contains the current component (signal component) derived from the reaction between GDH in an activated status that is contained in the first enzyme-imnpbilized portion 43A and the glucose. If the interstitial liquid contains an interference substance such as an ascorbic acid which affects the measurement of the glucose concentration, the first response current contains another signal component derived from (nonenzymatic reaction) reaction differing from the enzymatic reaction as influences of the interference substance.

By contrast, since the GDH in the second enzyme-immobilized portion 43B has been deactivated, the second response current contains no signal components derived from the reaction between the GDH and the glucose and contains only a signal component derived from the nonenzymatic reaction. Accordingly, when the signal component derived from the enzymatic reaction is defined as "m" and the signal component derived from the reaction other than the enzymatic reaction is defined as "n", a first response current value "y" and a second response current value "y'" (y and y' are functions of time "t") may be expressed by the following linear functions.

$$y(t)=m(t)+n(t) \quad \text{(Formula 1)}$$

$$y'(t)=n(t) \quad \text{(Formula 2)}$$

Hence, the control unit 12 subtracts the second response current value from the first response current value according to the formulae 1 and 2. Thereby, the signal component "n" derived from the nonenzymatic reaction may be removed from the first response current value.

The control unit 12 executes, based on the first response current value (corrected current value) from which the signal component "n" is removed, processes of computing the glucose concentration by employing a known technique (algorithm), and calculates the glucose concentration for the time (t) (Step S05). For example, the storage 13 of the control computer 3 previously retains calibration curve data of the glucose concentration corresponding to the GDH immobilized to the first enzyme-immobilized portion 43A, and the control unit 12 computes the glucose concentration by use of the calibration curve indicated by the calibration curve data. Alternatively, the control unit 12 computes the glucose concentration by substituting the first response current value corrected into a predetermined arithmetic formula for the glucose concentration.

The communication unit 10 transmits the computed result of the glucose concentration computed to the display unit 14 via a communication link 18 established between the display unit 14 and the communication unit 10 (Step S06). Thereafter, the control unit 12 determines whether the measurement is finished or not, and, if finished, terminates the processing based on the processing flow in FIG. 4. Whereas if not finished, the processing loops back to Step S02. With this operation, the glucose concentration is continuously measured till a trigger to finish the measurement such as inputting the measurement end instruction is inputted to the control computer 3 via the input device. The display unit 14 continuously receives the measured results of the glucose concentrations from the monitoring apparatus 1 and is thereby enabled to create a graph by plotting time-based variations in glucose concentration and to display the graph on the display screen (the display panel 15).

According to the first embodiment, the signal component derived from the non-enzymatic reaction acquired as the second response current value is removed from the first response current value. Hence, the first response current value is corrected to the response current value based on the signal component derived from the actual enzymatic reaction. The glucose concentration is calculated by use of the corrected response current value. Therefore, it may obtain the glucose concentration with the accuracy improved.

The first embodiment may be modified as follows. In the first embodiment, the enzyme of the enzyme-immobilized portion 43B corresponding to the second working electrode 42B is deactivated by electrification of the overcurrent to the second working electrode 42B, however, the enzyme may also be deactivated otherwise. For example, the enzyme-immobilized portion 43B may also be formed by dispensing the enzyme (GDH) with the reaction on the glucose being deactivated by heating. If possible, before attaching the monitoring apparatus 1 and the glucose sensor 4 to the examinee, it is considered that the enzyme of the enzyme-immobilized portion 43B is also deactivated by heating the enzyme-immobilized portion 43B.

Alternatively, the second enzyme-immobilized portion 43B may also be formed by employing the enzyme (GDH) of which the composition is pulverized (ground down) to such an extent as to deactivate the reaction on the glucose. Further alternatively, the enzyme of the second enzyme-immobilized portion 43B may also be set in the deactivated state when measured in a way that adds a substance (e.g., sodium azide) which accelerates or hinders the deactivation of the enzyme reaction to the second enzyme-immobilized portion 43B in the process of manufacturing the glucose sensor 4 or before measuring the glucose concentration. Thus, before starting the measurement, in the case of performing the enzyme deactivation process, it is feasible to omit the overcurrent electrification process as in step S01 depicted in FIG. 4 and the switch SW used for the overcurrent electrification process.

Moreover, the first embodiment has demonstrated the example of using the GDH as the enzyme, however, glucose oxidase (GOD) may be applied as a substitute for the GDH. Further, the first embodiment has exemplified the glucose as the specified ground substance, however, for the purpose of detecting a physical quantity of another, specified ground substance, the physical quantity with the accuracy improved may be acquired by employing the biosensor and the monitoring apparatus that have the configurations in the first embodiment in a manner that measures a biocatalyst corresponding to another specified ground substance.

Moreover, in the first embodiment, the response current value is corrected by subtracting the second response, current value from the first response current value, however, the glucose concentration with the improved accuracy may also be acquired by obtaining the corrected glucose concentration in a manner that acquires the computed results of the glucose concentrations based on the first response current value and the second response current value and subtracts the computed result of the glucose concentration based on the second response current value from the computed result of the glucose concentration based on the first response current value.

[Second Embodiment]

Next, a second embodiment of the present invention will be discussed. The second embodiment has the configuration common to the first embodiment, and hence the discussion will focus on points different from the first embodiment, and the common points (components) are marked with the same numerals and symbols, of which the explanations are omitted.

The physical configurations of the biosensor (the glucose sensor) and the monitoring apparatus 1 in the second embodiment may involve applying what has described in the first embodiment. The second embodiment is different from the first embodiment in terms of configurations of the first enzyme-immobilized portion 43A and the second enzyme-immobilized portion 43B of the biosensor (glucose sensor) 4.

To be specific, in the second embodiment, the enzymes (GDH) exhibiting a different calibration curve are applied as the enzymes (GDH) contained in the first enzyme-immobilized portion 43A and the second enzyme-immobilized portion 43B, respectively. An example in the second embodiment is that the wild (natural) GDH is applied as the GDH applied to the first enzyme-immobilized portion 43A, and mutant GDH, into which the wild GDH undergoes a genetic modification, is applied as the GDH applied to the second enzyme-immobilized portion 43B.

Figure 5:
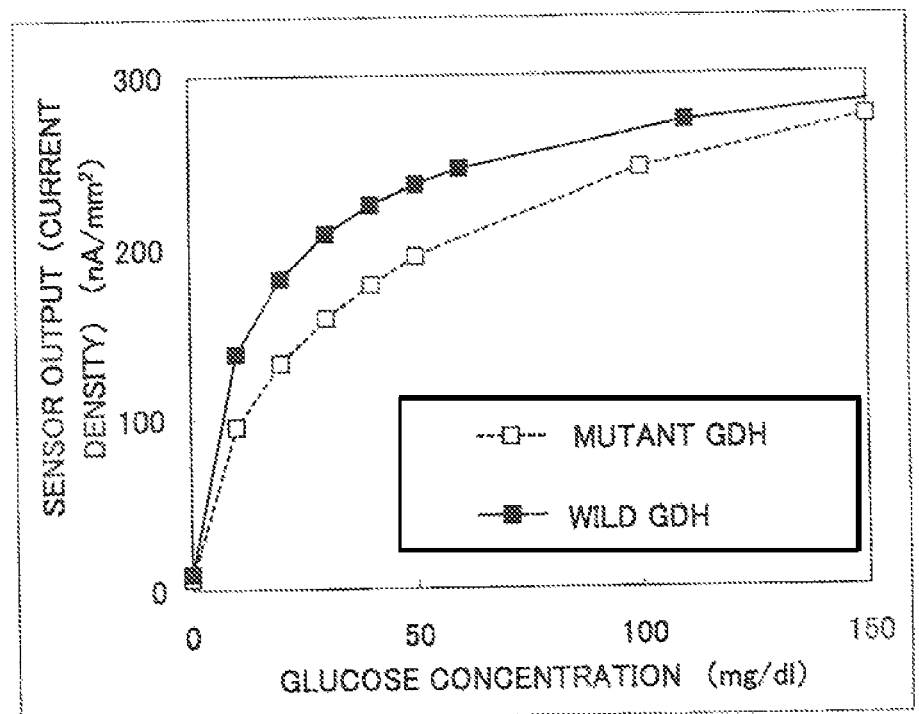
FIG. 5 is a graphic chart showing a relation between response currents coming from first and second working electrodes and a glucose concentration in a second embodiment.

The GDH (a first enzyme: a first biocatalyst) applied to the first enzyme-immobilized portion 43A and the GDH (a second enzyme: a second biocatalyst) applied to the second enzyme-immobilized portion 43B are different in their Michaelis constants Km. FIG. 5 illustrates a relation (calibration curve) between each sensor output (a response current density) and the glucose concentration in the case of providing the first working electrode 42A and the second working electrode 42B to which the first enzyme and the second enzyme are immobilized.

As depicted in the graph of FIG. 5, the calibration curve of the first working electrode 42A to which the first enzyme (the wild GDH) is applied, is different from the calibration curve of the second working electrode 42B to which the second enzyme (the mutant GDH) is applied, and it is thus understood that the different calibration curves are formed. In FIG. 5, a black plot represents the wild GDH, while a white plot represents the mutant GDH. Note that FIG. 5 indicates an example in which the calibration curve of the first enzyme (the wild GDH) is given by y=0.8x, while the calibration curve of the second enzyme (the mutant GDH) is given by y'=0.6x. The symbols y and y' denote the response current values, a value "x" represents the glucose concentration, and values "0.8" and "0.6" indicate calibration curve coefficients.

Thus, in the second embodiment, the calibration curve of the first working electrode 42A where the first enzyme is disposed is different from the calibration curve of the second working electrode 42B where the second enzyme is disposed, and data on the respective calibration curves (the calibration curve coefficients) are previously stored in the storage 13 (e.g., the ROM) of the control computer 3, of the monitoring, apparatus 1.

Figure 6:
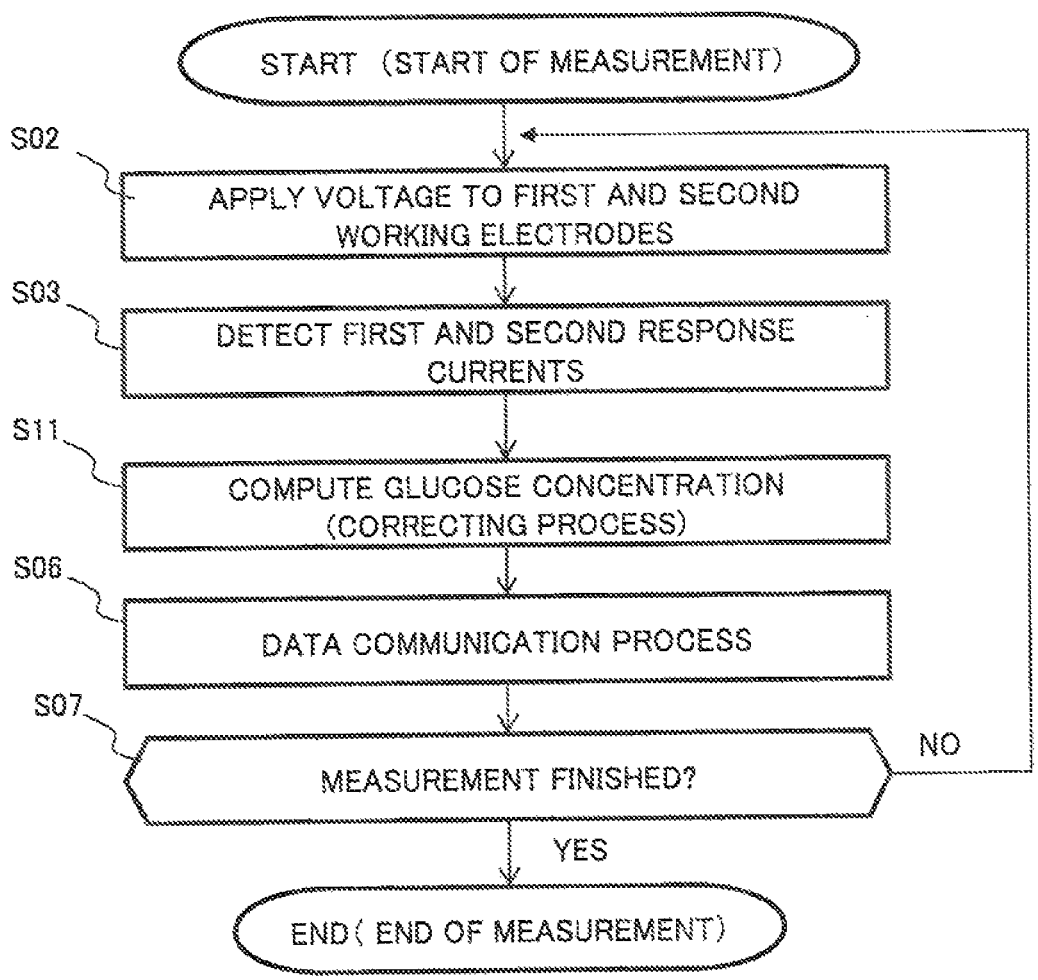
FIG. 6 is a flowchart showing the program processing of the control unit in the second embodiment.

Further, in the second embodiment, a method of correcting the glucose concentration, is different from the method in the first embodiment. FIG. 6 is a flowchart indicating an example of the processing of the control computer 3 according to the second embodiment.

The processes illustrated in FIG. 5 are different from those in the first embodiment in terms of excluding Step S01 but executing Step S11 (a glucose concentration computing (correcting) process) in place of Steps S04 and S05.

In Step S11, the control unit 12 acquires the first, response current value and the second response current value each obtained by the potentiostat 3A. The control unit 12 obtains the glucose concentration x at the unit time t, which is corrected based on the following formula 3.

$$x(t)=(y(t)-y'(y))/(a-b) \qquad \text{(Formula 3)}$$

where y represents the first response current value (the signal acquired from the first working electrode 42A), and y' denotes the second response current value (the signal obtained from the second working electrode 42B). Moreover, a value "a" stands for the calibration curve coefficient corresponding to the first enzyme (the wild GDH), and a value "b" represents the calibration curve coefficient corresponding to the second enzyme (the mutant GDH).

The formula 3 is acquired based on the following idea. Namely, the first working electrode 42A (the enzyme-immobilized portion 43A) and the second working electrode 42B (the enzyme-immobilized portion 43B) come to the state of being immersed in the interstitial liquid under the same condition. It may be therefore considered that the first response current and the second response current equally contain the signal component derived from the nonenzymatic reaction such as the interference substance reaction. Hence, the first response current y and the second response current y' may be expressed by the linear functions as by the following formulae 4 and 5.

$$y(t)=ax+c \qquad \text{(Formula 4)}$$

$$y'(t)=bx+c \qquad \text{(Formula 5)}$$

where values "a" and "b" are the calibration curve coefficients, and a value "c" is the signal component derived from the nonenzymatic reaction. When transformed by use of the formulae 4 and 5, it is feasible to acquire the formula 3 defined as the formula for calculating the glucose concentration described above.

The control unit 12 may acquire the glucose concentration x from which to remove the signal component c derived from the nonenzymatic reaction by substituting the first response current y and the second response current y' into the formula 3 (the calibration curve coefficients a and b are already known and retained beforehand in the storage unit 13).

Figure 7:
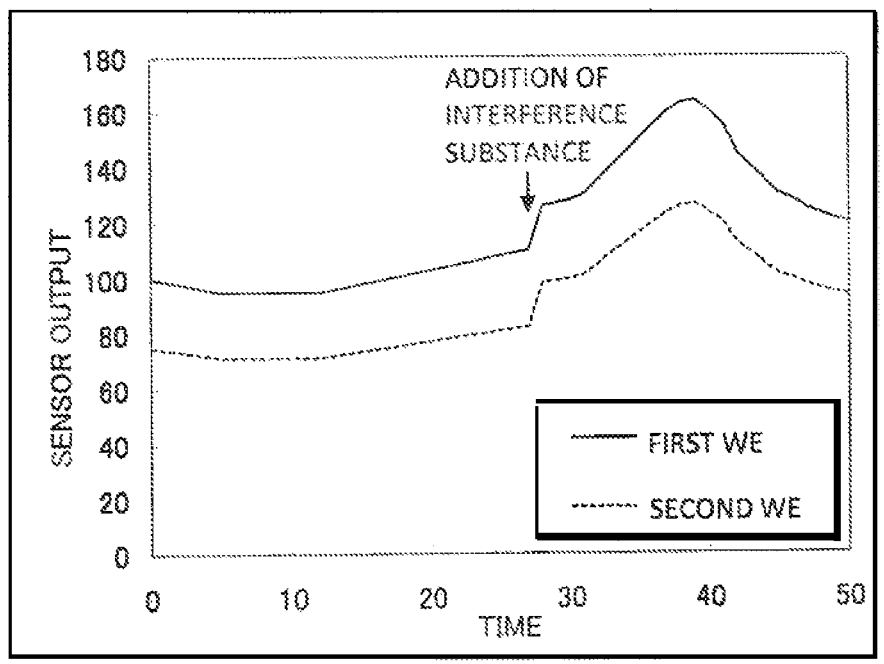
FIG. 7 is a graphic chart showing an example of a simulation experiment for demonstrating operations and effects in the second embodiment and showing time-based variations in response current.
Figure 8:
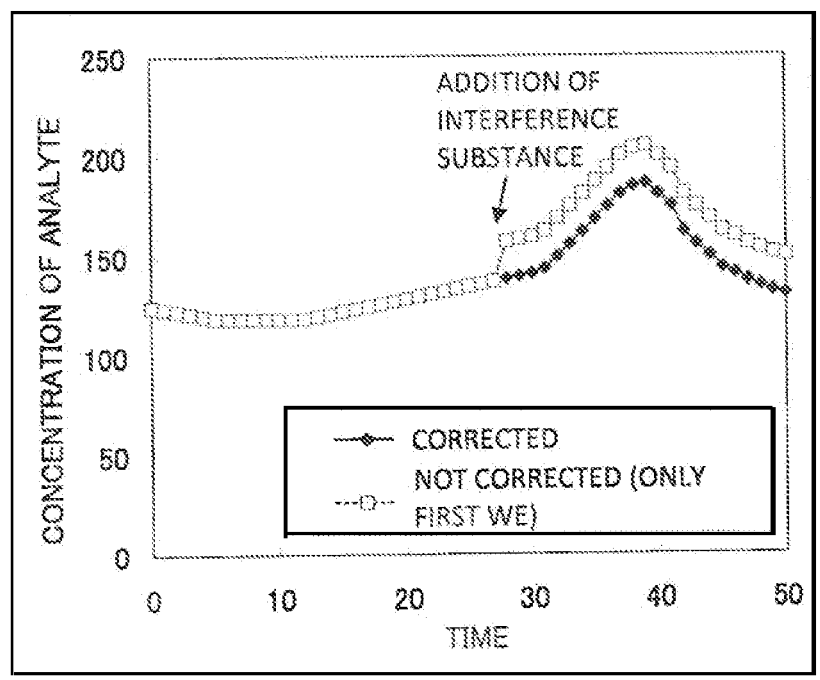
FIG. 8 is a graphic chart showing an example of the simulation experiment for demonstrating the operations and the effects in the second embodiment and showing time-based variations in concentration of an analyte.

FIGS. 7 and 8 illustrate graphs showing examples of simulation experiments for demonstrating the operations and the effects in the second embodiment. FIG. 7 illustrates the graphs showing time-based variations of sensor outputs (the first response current (the first working electrode 42A), the second response current (the second working electrode 42B)) of the glucose sensor 4 using the first enzyme and the second enzyme explained in FIG. 5. The sensor outputs indicate current signals detected by the biosensor (the glucose sensor 4 in the second embodiment). In FIG. 7, the graph of the sensor output expressed by a solid line represents the first response current, while the graph of the sensor output expressed by a broken line represents the second response current. In the simulation experiment shown in FIG. 7, a liquid containing none of the interference substance is applied as a test liquid defined as the body fluid. Accordingly, the first response current and the second response current can be considered to be the response currents in the case of not containing any signal components derived from the nonenzymatic reaction.

In the graphs of FIG. 7, the interference substance (which is the ascorbic acid in this experiment) is added to within the test target body fluid at a time-count of approximately 28. As a result, the signal component derived from the reaction between the ascorbic acid and the electrode, i.e., the signal component derived from the nonenzymatic reaction is added to the response current, with the result that the first response current and the second response current rise respectively. It is recognized from the graphs of FIG. 7 that the rise in current due to the addition of the interference substance, i.e., the signal component c derived from the nonenzymatic reaction is contained equally in the first response current and the second response current. It is thereby understood that the first response current in FIG. 7 is expressed by the formula 4 and the second response current is expressed by the formula 5.

FIG. 8 illustrates the graph showing the time-based variations of the analyte (which is the glucose in this example) concentration in the simulation experiment, in which the glucose concentration corresponds to the response current shown in FIG. 7. The white plot in FIG. 8 indicates the glucose, concentration acquired based on the first response current from the first working electrode 42A. The white plot shows that the glucose concentration acquired by the computation rises together with the increase in the first response current due to the addition of the interference substance (at the time-count of about 28).

By contrast, the black plot, which is subsequent, substantially in continuation from the point of time when adding the interference substance, to the white plot, indicates the post-correction glucose concentration calculated, by use of the formula 3 described above. Thus, it is understood that the correction value is acquired from the black plot, which is substantially equal to the computed value of the glucose concentration based on the first response current that will have been detected from the first working electrode 42A unless the interference substance is added.

Hence, the glucose sensor 4 and the monitoring apparatus 1 according to the second embodiment enable the acquisition of the correction value from which to properly remove, even when the interference substance contained in the interstitial liquid (the body fluid) affects the response current value due to the reaction of the interference substance on the electrode, this affection. Namely, it is possible to obtain the measurement result of the glucose concentration with the high accuracy.

The second embodiment may be modified as follows. To be specific, the second embodiment involves using the two enzymes having the different Michaelis constants Km as the first and second enzymes (the first and second biocatalysts) exhibiting the different calibration curves. The two enzymes exhibiting different maximum speeds Vmax may be also applied in terms of differentiating the calibration curves due to the difference between the reaction speeds. Namely, it is feasible to apply the two enzymes having the different values of at least one of Km (Michael is constant) and Vmax (maximum speed).

Moreover, it may be sufficient that the calibration curves are different from each other, and therefore the same type of enzymes are employed on one hand, while the total reaction activation quantities on the first working electrode 42A and the second working electrode 42B may be differentiated by making different the enzyme allocation, quantities (the enzyme quantities) for the first working electrode 42A (the first enzyme-immobilized portion 43A) and the second working electrode 42B (the second enzyme-immobilized portion 43B), respectively.

Alternatively, the same type of enzymes are used on one hand, while the contact area between the enzyme and the body fluid is differentiated with respect to the first working electrode 42A (the first enzyme-immobilized portion 43A) and the second working electrode 42B (the second enzyme-immobilized portion 43B), whereby the calibration curves may be made different.

Further, the different types of enzymes may also be used between the working electrodes in terms of differentiating the calibration curves. For instance, it is considered that the GDH is applied to one of the first, working electrode 42A (the first enzyme-immobilized portion 43A) and the second working electrode 42B (the second enzyme-immobilized portion 43B), and the GOD (glucose oxidase) is applied to the other working electrode.

Note that the second response current obtained from the second working electrode 42B of the glucose; sensor 4 (the biosensor) in the first embodiment does not contain the signal component derived from the enzymatic reaction, and it can be therefore considered that "bx (at least one of the ground substance concentration x and the calibration curve coefficient b) in the formula 5 is zero. Hence, the proper glucose concentration may be measured based on the program processing (the computation in the formula 3) of the control unit 12 in the second embodiment by use of the glucose sensor 4; in the first embodiment.

The configurations according to the first and second embodiments discussed above can be combined appropriately within the range that does not deviate from the purpose of the present invention.

FIRST WORKING EXAMPLE

Next, working examples of the present invention will be described. The working examples involve creating a 4-electrode system including two working electrodes WE1, WE2, a reference electrode RE and a counter electrode CE. Specifically, a metal layer of Au is deposited up to 5 nm by sputtering on a polymide base material (polyether-imide (PEI), 100 μm). Three areas, insulated from each other are formed in such a manner that the metal layer undergoes an insulating process, then printing is effected on the two areas among these three metal layer areas by use of a carbon ink, and the printed areas are dried for 30 min under an environment of 110° C., thereby manufacturing the two working electrodes WE1, WE2. The remaining area is formed as the counter electrode CE.

Furthermore, to make the reference electrode RE, the printing is effected on the remaining metal layer area (the counter electrode CE) by using, a silver-silver chloride (Ag/AgCl) ink, and the printed area is dried for 30 minutes under the environment of 150° C. The silver-silver chloride ink involves using [E2414] made by ERCON Corp.

A GDH solution mixed with, glucose dehydrogenase (GDH) as the enzyme, sodium acid phosphate (pH5.8) serving as a pH adjustor and glutaraldehyde (GA) serving as a crosslinker is produced as a reagent, which is dispensed to the working electrode WE1 and the working electrode WE2; At this time, a final concentration (f.c.) of the GDH is on the order or 1250 U/mL, and the final concentration of sodium acid phosphate is 50 mM. Further, as a crosslinking condition, the reaction time, 45 minutes, and the reaction temperature, 20° C., are applied.

After dispensing the GDH solution of 0.32 μL to the working electrode WE1 and drying the solution, the GDH is deactivated by performing a 10-min drying process under the environment of 80° C. Thereafter, the GDH solution of 0.32 μL is dispensed to the working electrode WE2 and then dried. The working electrode WE1 is thus formed as a heat-deactivated electrode in. which the enzymatic reaction of the GDH is deactivated by heat, while the working electrode WE2 is formed as the activated working electrode exhibiting the GDH activation.

A response sensibility to the glucose and a response sensibility to an ascorbic acid (AsA) defined as the interference substance are examined by a chronoamperometry method of applying a potential difference of 400 mV to the electrode system in a way that employs the electrode system described above.

To begin with, a method of measuring the response sensibility to the glucose (Glu) involves electrically connecting the working electrode (heat-deactivated electrode) WE1, the working electrode (activated working electrode) WE2 and the counter electrode CE of the electrode system and the potentiostat and immersing the electrode system in a 0.1 M phosphate buffer solution (pH7.0) serving as a measurement liquid. Then, a 2.0 M glucose solution is dripped in the buffer solution while a constant voltage (400 mV vs Ag/AgCl) is applied to the working electrode WE1 and the working electrode WE2. Steady-state current densities (nA/mm$^2$) when the final concentration of the glucose is 100 mg/dL are measured. The steady-state current density corresponds to the response sensibility.

Figure 9:
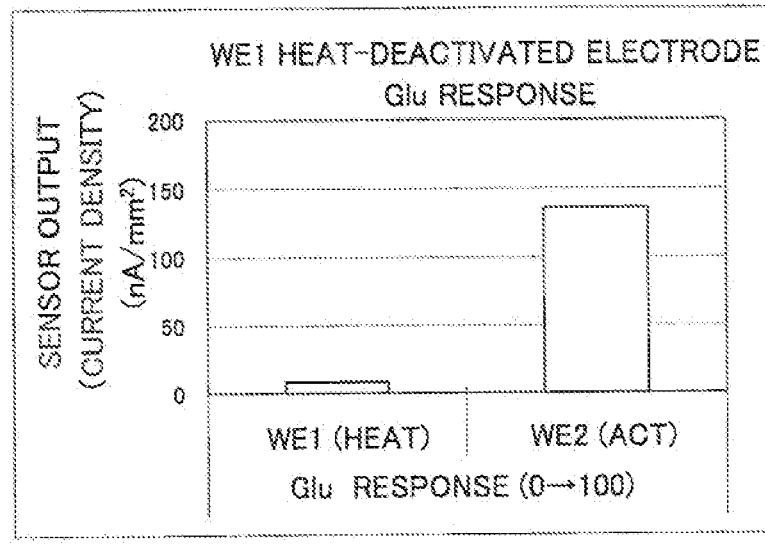
FIG. 9 is a graphic chart illustrating a working example of the present invention and showing a response current density when adding the glucose.

FIG. 9 shows a measurement result of the sensor outputs (current densities) to the glucose. As understood from FIG. 9, it is confirmed in the activated working electrode WE2 that the response current density based on the enzymatic reaction of the GDH and, by contrast, almost no response current density is seen in the heat-deactivated electrode WE1 in which the GDH is deactivated: This leads to a confirmation that the GDH on the electrode WE1 is deactivated.

Next, the method of measuring the response sensibility to the ascorbic acid (AsA) involves, electrically connecting the. working electrode (heat-deactivated electrode) WE1, the working electrode (activated working electrode) WE2 and the counter electrode of the electrode system and the potentiostat and immersing the electrode system in the 0.1 M phosphate buffer solution (pH7.0). Then, the steady-state current densities (nA/mm$^2$) when the final concentration of AsA is 1.0 mg/dL are measured by adding the 10 mg/mL ascorbic acid (AsA) in the buffer solution while applying the constant voltage (400 mV vs Ag/AgCl) to the heat-deactivated electrode WE1 and the activated working electrode WE2. The steady-state current density corresponds to the response sensibility.

Figure 10:
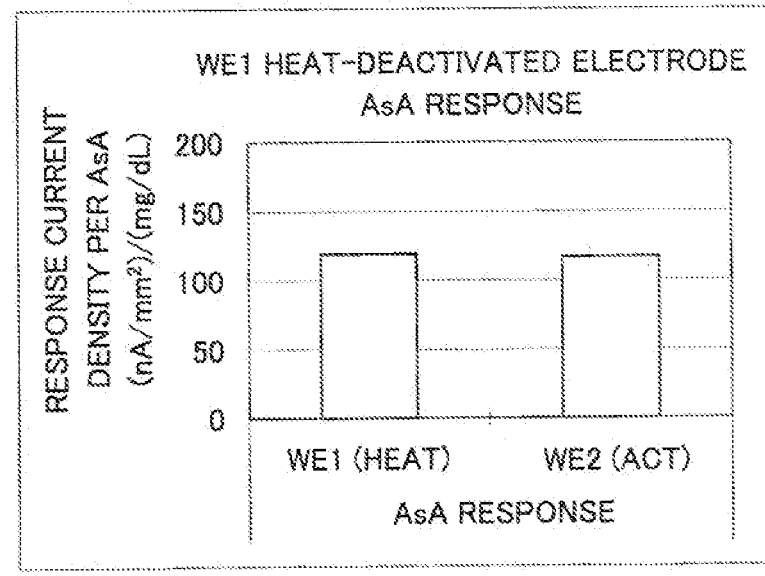
FIG. 10 is a graphic chart illustrating the working example of the present invention and showing the response current density when adding an ascorbic acid.

FIG. 10 shows, a measurement result of the response sensibility to AsA. As understood from FIG. 10, is confirmed in both of the heat-deactivated electrode WE1 and the activated working electrode WE2 detect response current densities, each of which has the same level substantially, derived from the electrode reaction of AsA.

Moreover, it is checked how the ascorbic acid affects in the case of adding the ascorbic acid (AsA) during the measurement of the response sensibility of the glucose. The measurement method involves electrically connecting the working electrode (heat-deactivated electrode) WE1, the working electrode (activated working electrode) WE2 and the counter electrode of the electrode system and the potentiostat and immersing the electrode system in the 0.1 M phosphate buffer solution (pH7.0). Then, the glucose solution is continuously dripped in the buffer solution at a point of 300 second elapse time since the start of the measurement while the constant voltage (400 mV vs Ag/AgCl) is applied to the heat-deactivated electrode WE1 and the activated working electrode WE2, in order to measure the steady-state current densities (nA/mm$^2$) in case where the final concentration of the glucose becomes 100 mg/dL.

Thereafter, the steady-state current densities (nA/mm$^2$) in a case where the final concentration of AsA becomes 1.0 mg/dL are measured by adding the 10 mg/mL ascorbic acid (AsA) in the buffer solution at a point of 400-sec elapse time since the start of the measurement.

Thereafter, the steady-state current densities (nA/mm$^2$) in a case, where the final, concentration of ASA becomes 2.0 mg/dL are measured by adding the 10 mg/mL ascorbic acid (AsA) in the buffer solution at a point of 500-sec elapse time since the start of the measurement.

Figure 11:
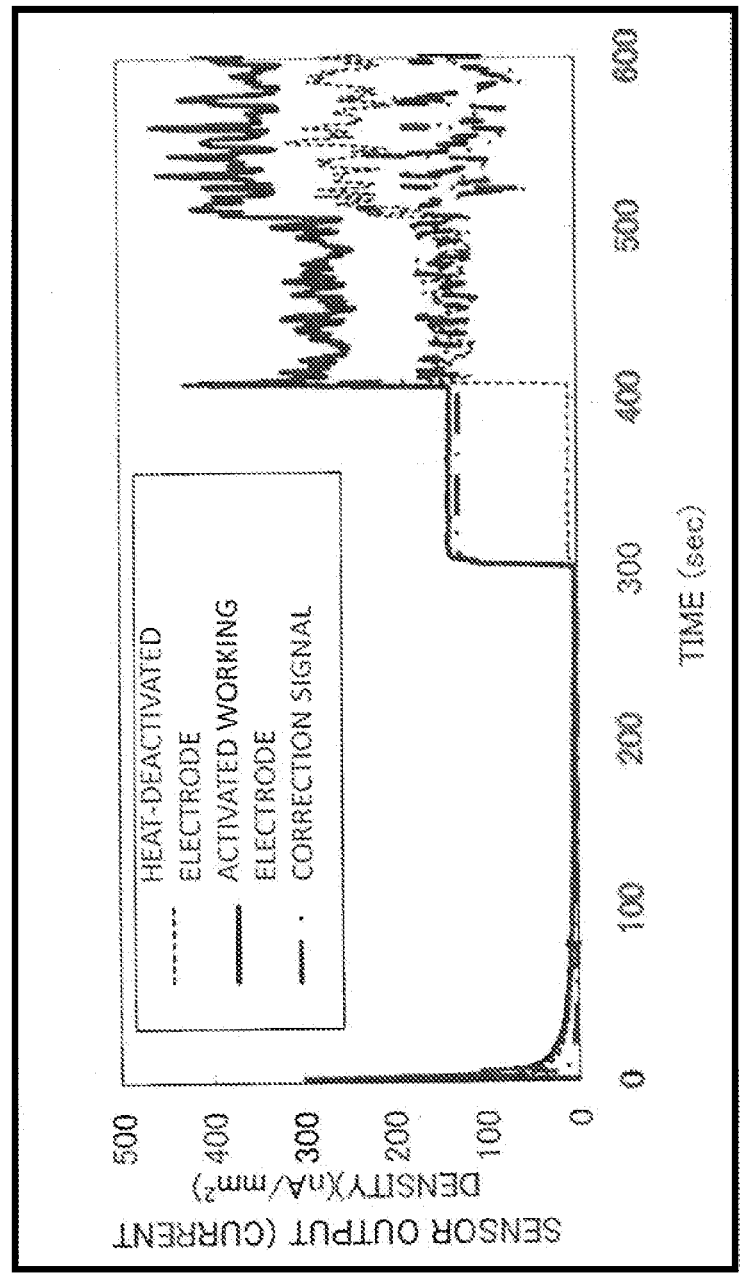
FIG. 11 is a graphic chart illustrating the working example of the present invention and showing the response current density when adding the glucose, how the addition of the ascorbic acid affects the response current density and the time-based variations in correction current density corrected by a correcting method according to the present invention.

FIG. 11 shows a measurement result of time-based variations in sensor outputs (response current densities (nA/mm$^2$)) of the heat-deactivated electrode WE1 and the activated working electrode WE2. In FIG. 11, the graph of the solid line represents the sensor output (the response current density) of the activated working electrode WE2, while the graph of the broken line, represents the sensor output (the response current density) of the heat-deactivated electrode WE1. Further, the graph of one-dotted chain line represents time-based, variations in current density (corrected, value) corrected by the correcting technique explained in the first embodiment.

The response current due to the enzymatic reaction of the GDH is observed from the activated working, electrode WE2 when dripping (adding) the glucose at the predetermined timing (at the point of 300-sec elapse time) since the start of the measurement, and, by contrast, it is confirmed that a minute response current is detected from the heat-deactivated electrode WE1.

Thereafter, with the AsA addition at the predetermined timing (at the point of 300-sec elapse time) since the start of the measurement, it is confirmed that the current density as the signal component derived from the nonenzymatic reaction due to the electrode reaction of AsA is detected substantially equally from both of the heat-deactivated electrode WE1 and the activated working electrode WE2.

Moreover, with a doubled-increase in AsA concentration at the predetermined timing (at the point of 500-sec elapse time) since the start of the measurement, it is confirmed that the response currents of both of the electrodes WE1 and the electrode WE2 increase. Then, it is confirmed that the correction signal (the correction value) acquired by subtracting the response current density of the electrode WE1 from the response current density of the electrode WE2 shows the current density smaller than the activated working electrode WE2 has, over a period (400-500 sec) for which the final concentration of AsA is 1.0 mg/dL and a period (from 500 sec onward) for which the final concentration of AsA is 2.0 mg/dL. It is thereby confirmed that the acquisition of the correction value of the response current enables, the measurement of the glucose concentration with the restrained affection of the ascorbic acid.

Moreover, it is ascertained from the measurement result in FIG. 11 that though the amplitude, rises due to the increase in addition quantity of AsA, there are deflections in the plus-and-minus directions of which a benchmark is the response current density (approximately 150 nA/mm$^2$) of the working electrode WE2 in the ease of the addition of only the glucose (300-400 sec) and, for example, the response current density; approximate to the density when adding none of the ascorbic acid can be computed by taking the time-based average of the correction values.

SECOND WORKING EXAMPLE

Next, a second working example of the present invention will be discussed. The second working example acquires data for correcting the affection of the interference substance in the response of a main electrode that is, adjusted by the natural (wild type) enzyme by use of the response of a sub-electrode that is adjusted by the mutant (genetic modification (genetic transmutation)) enzyme.

In The second, working example, a main sensor (Main WE) including 3-electrode system containing the working electrode WE1, the reference electrode RE and the counter electrode CE and a sub-sensor (Sub WE) including the 3-electrode system containing the working electrode WE2, the reference electrode RE and the counter electrode CE. Herein, the working electrode WE1 of the main sensor (Main WE) and the working electrode WE2 of the sub-sensor (Sub WE) are formed by the same area to enable relatively comparing sensor outputs (current values) of the main sensor and the sub-sensor.

Each of the main sensor and the sub-sensor is created as follows. To be specific, the metal layer of Au is deposited up to 5 nm by sputtering; on the polyimide base material (polyether-imide (PEI), 100 μm). Two areas insulated, from each other are formed in such a manner that this metal layer undergoes the insulating, process, then printing is effected on one area of the two metal layer areas by use of the carbon ink, and the printed area is dried for 30 min under the environment of 110° C., thereby manufacturing the working electrode WE1 (the working electrode WE2). The remaining area is formed as the counter electrode CE.

Furthermore, the printing is effected on the remaining metal layer area (the counter electrode CE) by using the silver-silver chloride (Ag/AgCl) ink, and the printed area is dried for 30 min under the environment of 150° C., thereby manufacturing the reference electrode RE. The silver-silver chloride ink involves using [E2414] made by ERCON Corp.

The GDH solution mixed with glucose dehydrogenase (GDH) as the enzyme, sodium acid phosphate (pH5.8) serving as the pH adjustor and glutaraldehyde (GA) serving as the crosslinker is produced as the reagent, which is dispensed to the working electrode WE1 of the main sensor and the working electrode WE2 of the of the sub-sensor. At this time, the final concentration (f.c.) of the GDH is on the order or 1250 U/mL, and the final concentration of sodium acid phosphate is 50 mM. Further, the reaction time, 45 minutes, and the reaction temperature, 20° C., are applied as the crosslinking condition.

The wild GDH is used as the GDH in the reagent dispensed to the working electrode WE1 of the main sensor, while the mutant GDH is employed as the GDH in the reagent dispensed to the working electrode WE2 of the sub-sensor. Thus, the wild GDH solution for the main sensor and the mutant GDH solution for the sub-sensor are produced.

The wild GDH solution of 0.32 μL is dispensed to the working electrode WE1 of the main sensor and then dried. On the other hand, the genetic modification GDH solution of 0.32 μL is dispensed to the working electrode WE2 of the sub-sensor and then dried. Thus, the main sensor (Main WE) to which the wild GDH is dispensed and the sub-sensor (Sub WE) to which the mutant GDH is, dispensed are obtained.

Figure 12:
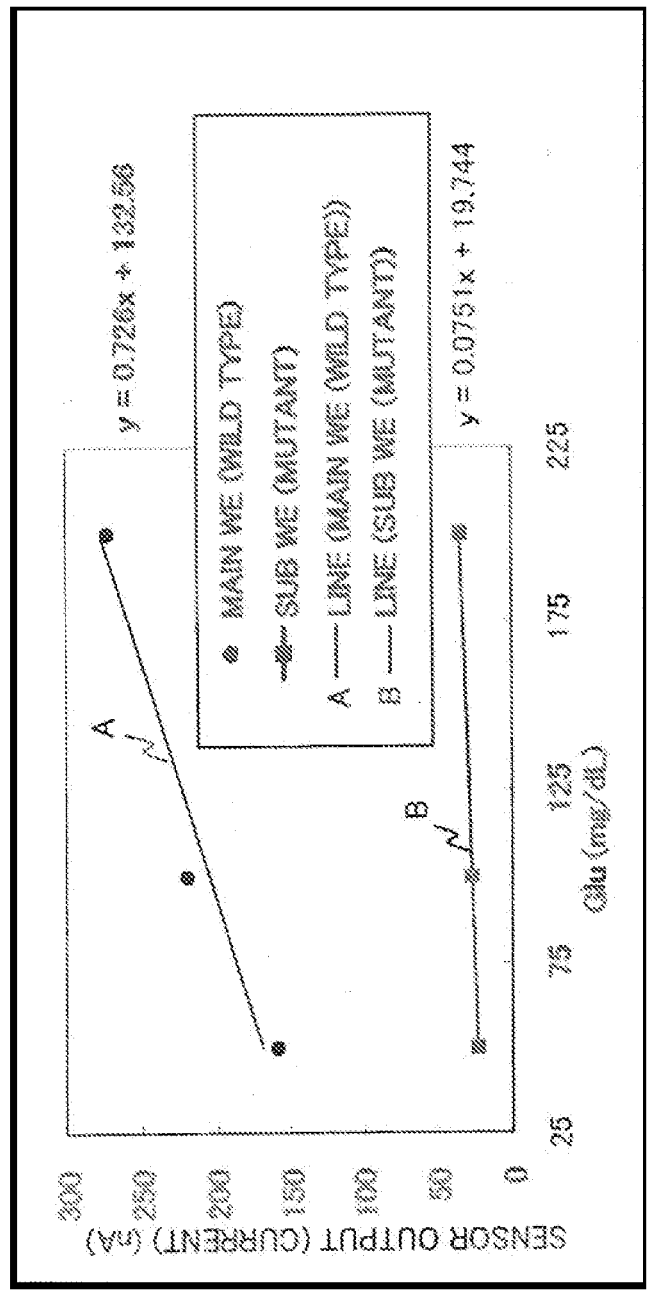
FIG. 12 is a graphic chart according to a second working example of the present invention, showing calibration curves with respect to the glucose by use of a main sensor (Main WE) adjusted by natural GDH and a sub-sensor (Sub WE) adjusted by genetic modification GDH.

The calibration curves of the glucose are generated with respect to the main sensor (Main WE) and the sub-sensor (Sub WE). FIG. 12 shows the result thereof. The calibration curve obtained by the sensor output of the main sensor is indicated by a graph A in FIG. 12, and the calibration curve obtained by the sensor output of the sub-sensor is indicated by a graph B. Both of the main sensor and the sub-sensor exhibit such a characteristic that the sensor output (current value: the response sensibility) rises corresponding to the increase in glucose concentration.

The response sensibility to the glucose and the response sensibility to the ascorbic acid (AsA) defined as the interference substance are examined by the chronoamperometry method of applying the potential difference of 400 mV to the electrode system employing the main sensor and the sub-sensor.

To start with, the method of measuring the response sensibility to the glucose (Glu) involves electrically connecting the working electrode WE1 (working electrode WE2) and the counter electrode CE to the potentiostat with respect to each of the main sensor and the sub-sensor. Next, each of the main, sensor and the sub-sensor is immersed in a glucose solution of 200 mg/dL, and the constant voltage (400 mV vs Ag/AgCl) is applied respectively to the working electrode WE1 and the working electrode WE2, thus starting the measurement.

Thereafter, each of the sensor outputs (current values (nA)) of the main sensor and the sub-sensor in a case where the final concentration of the glucose becomes 100 mg/dL is measured by adding a 0.1 M phosphate buffer solution (pH7.0) to within the glucose solution. Moreover, the sensor outputs (current values (nA): referred to as a value "Y") of the main sensor and the sub-sensor in a case where the final concentration of AsA becomes 1.0 mg/dL are measured by adding the 10 mg/mL ascorbic acid (AsA) after an elapse of a predetermined period of time since the start of the measurement.

Figure 13:
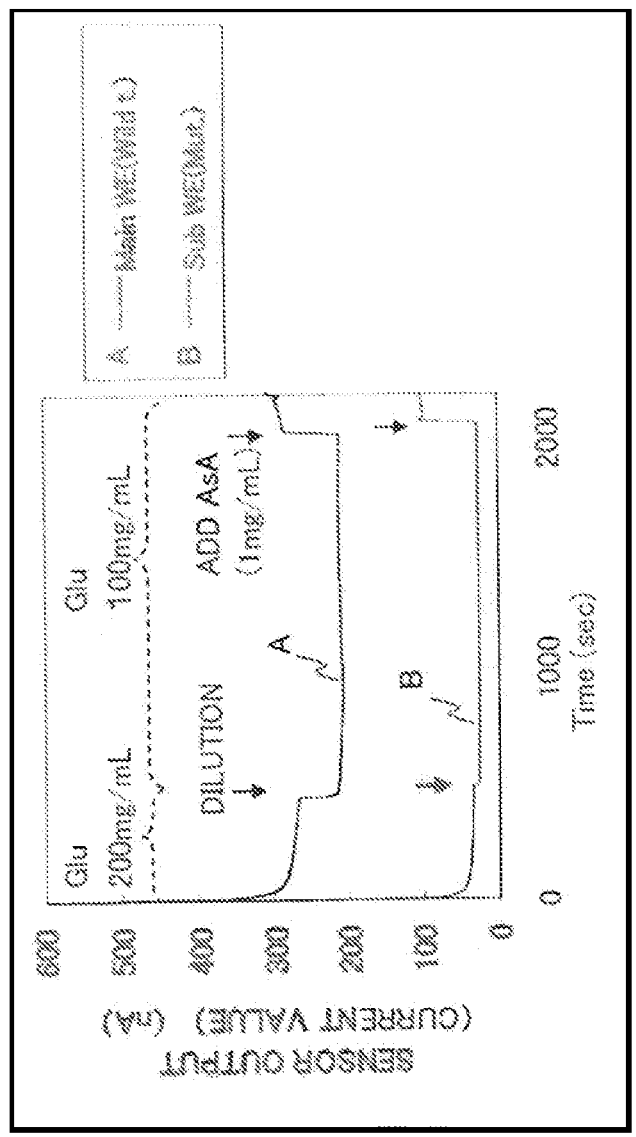
FIG. 13 is a graphic chart according to the second working example of the present invention, showing, transitions of sensor outputs (response sensibilities) of the main sensor and the sub-sensor.

FIG. 13 shows the measurement results. The measurement result of the main sensor is indicated by a graph A in FIG. 13, and the measurement result of the sub-sensor is indicated by a graph B. As understood from FIG. 13, it is ascertained that the sensor outputs of the main sensor and the sub-sensor exhibit the response current values based on the calibration curves in response to the dilution of the glucose solution with the addition of the buffer solution. Further, it is also confirmed that the response current values, each of which has the same level substantially, derived from the electrode reaction of AsA are detected from both of the working electrode WE1 and the working electrode WE2 due to the addition of AsA.

Figure 14:
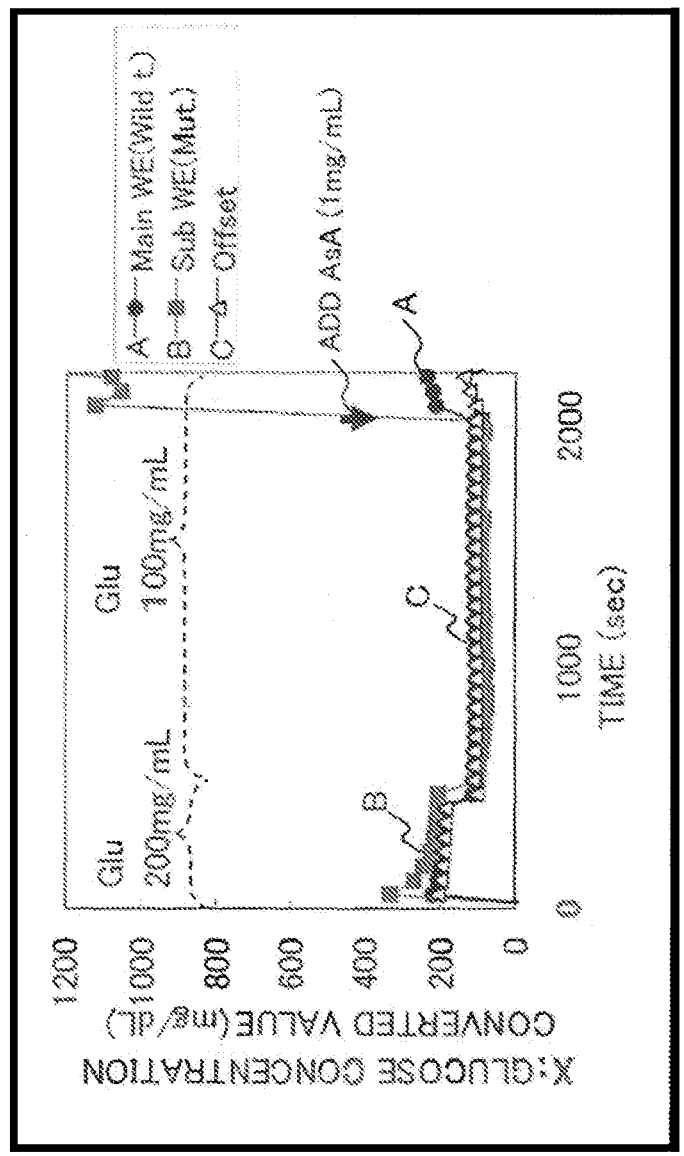
FIG. 14 is a graphic chart according to the second working example of the present invention, showing transitions of the glucose concentration corrected by use if the sensor output of the main sensor and the sensor output of the sub-sensor.

Moreover, the sensor outputs (values "Y") shown in FIG. 13 is converted into the glucose concentration "X" according to the calibration curve illustrated in FIG. 12, and the corrected value (corrected data) of the main sensor is obtained based on the above-mentioned (Formula 3) for acquiring the glucose concentration x(t) related to the correction explained in the second embodiment. The results are shown in FIG. 14. The measurement result of the main sensor (Main WE (Wild t.)) is indicated by a graph A (a circle plot) in FIG. 14, the measurement result of the sub-sensor (Sub WE (Mut.)) is indicated by a graph b (a square plot), and the correction data (Offset) is indicated by a graph C (a triangle plot). However, the graphs A and B exhibited in FIG. 14 indicate results (values "X") of the glucose concentration when current densities (nA/mm$^2$) obtained from each of the current value (value "Y") of the main sensor and the sub-sensor shown in FIG. 13 are used.

As recognized from FIG. 14, the X's value (A: the circle plot) obtained by the main sensor (Main WE) rises in a way that contains the AsA-derived component due to the addition of AsA, while the corrected X's value (C: the triangle plot) hardly rises even after adding AsA.

According to the second working example, it is confirmed that the glucose concentration can be measured in a manner that restrains the affection of AsA by use of the sensor including the working electrode WE1 to which the reagent containing the natural GDH is dispensed and the working electrode WE2 to which the reagent containing the genetic, modification GDH is dispensed.

What is claimed is:

1. A biosensor, comprising:
   a first working electrode on which is disposed a first biocatalyst with the property that it reacts with a specific ground substance;
   a second working electrode on which is disposed a second biocatalyst with the property that it also reacts with the specific ground substance; and
   at least one counter electrode for applying a voltage to the first working electrode and the second working electrode,
   wherein a rate of reaction of the first biocatalyst with the specific ground substance is different from a rate of reaction of the second biocatalyst with the specific ground substance, and
   wherein the first biocatalyst and the second biocatalyst are enzymes of the same type.

2. A biosensor, comprising:
   a first working electrode on which is disposed a first enzyme with the property that it reacts with a specific ground substance;
   a second working electrode on which is disposed a second enzyme with the property that it reacts with the specific ground substance; and
   at least one counter electrode for applying a voltage to the first working electrode and the second working electrode,
   wherein the second enzyme is obtained by genetic modification of the first enzyme so that a rate of reaction of the second enzyme with the specific ground substance is different from a rate of reaction of the first enzyme with the specific ground substance.

3. A biosensor in combination with a monitoring apparatus, wherein the biosensor comprises:
   a first working electrode on which is disposed a first biocatalyst with the property that it reacts with a specific ground substance;
   a second working electrode on which is disposed a second biocatalyst with the property that it also reacts with the specific ground substance; and
   at least one counter electrode for applying a voltage to the first working electrode and the second working electrode,
   wherein a reaction area on the first working electrode is different from a reaction area on the second working electrode, and
   wherein the monitoring apparatus comprises:
   a first detection unit which detects a first signal value from the first working electrode obtained by applying a voltage between the first working electrode and one of the counter electrodes;
   a second detection unit which detects a second signal value from the second working electrode obtained by applying a voltage between the second working electrode and one of the counter electrodes;
   a correction unit which corrects a concentration of the specific ground substance that is calculated from the first signal value by the second signal value; and
   an output unit which outputs the corrected concentration of the specific ground substance,
   wherein the first working electrode is used to detect the first signal value to calculate a concentration of the specific ground substance and the second working electrode is used to detect the second signal value to correct the concentration of the specific ground substance calculated from the first signal value,
   wherein the corrected concentration of the specific ground substance is obtained based on the formula:

$$x(t)=(y(t)-y'(t))/(a-b)$$

wherein in the formula, a first signal value y(t) at a certain point of time t is expressed by a linear function $$y(t)=ax(t)+c,$$

where a is a calibration curve coefficient corresponding to the first biocatalyst, x is a concentration of the specific ground substance and c is a signal component based on a substance excluding the specific ground substance in a body fluid;
   a second signal y'(t) at a certain point of time t is expressed by a linear function $$y'(t)=bx(t)+c,$$

where b is a calibration curve coefficient corresponding to the second biocatalyst, x is the concentration of the specific ground substance and c is the signal component; and
   a value of the signal component c in the first signal value y(t) is equal to a value of the signal component c of the second signal value y'(t).

4. A biosensor in combination with a monitoring apparatus, wherein the biosensor comprises:
   a first working electrode on which is disposed a first biocatalyst with the property that it reacts with a specific ground substance;
   a second working electrode on which is disposed a second biocatalyst with the property that it also reacts with the specific ground substance; and
   at least one counter electrode for applying a voltage to the first working electrode and the second working electrode,
   wherein a total reaction activity of the first working electrode is different from a total reaction activity of the second working electrode, and
   wherein the monitoring apparatus comprises:
   a first detection unit which detects a first signal value from the first working electrode obtained by applying a voltage between the first working electrode and one of the counter electrodes;
   a second detection unit which detects a second signal value from the second working electrode obtained by applying a voltage between the second working electrode and one of the counter electrodes; and a correction unit which corrects a concentration of the specific ground substance that is calculated from the first signal value by the second signal value; and an output unit which outputs the corrected concentration of the specific ground substance, wherein the first working electrode is used to detect the first signal value to calculate a concentration of the specific ground substance and the second working electrode is used to detect the second signal value to correct the concentration of the specific ground substance calculated from the first signal value, wherein the corrected concentration of the specific ground substance is obtained based on the formula $$x(t)=(y(t)-y'(t))/(a-b)$$

wherein in the formula, a first signal value y(t) at a certain point of time t is expressed by a linear function $y(t)=ax(t)+c$, where a is a calibration curve coefficient corresponding to the first biocatalyst, x is a concentration of the specific ground substance and c is a signal component based on a substance excluding the specific ground substance in a body fluid;

a second signal y'(t) at a certain point of time t is expressed by a linear function $$y'(t)=bx(t)+c,$$

where b is a calibration curve coefficient corresponding to the second biocatalyst, x is the concentration of the specific ground substance and c is the signal component; and a value of the signal component c in the first signal value y(t) is equal to a value of the signal component c of the second signal value y'(t), and wherein the first biocatalyst and the second biocatalyst are enzymes of the same type.

5. A monitoring apparatus, comprising:

a first detection unit which detects a first signal value from a first working electrode obtained by applying a voltage between the first working electrode and a counter electrode, wherein disposed on the first working electrode is a first biocatalyst with the property that it reacts with a specific ground substance;

a second detection unit which detects a second signal value from a second working electrode obtained by applying a voltage between the second working electrode and the counter electrode, wherein disposed on the second working electrode is a second biocatalyst with the property that it also reacts with the specific ground substance and has a rate of reaction different from that of the first biocatalyst;

a correction unit which corrects a concentration of the specific ground substance that is calculated from the first signal value by the second signal value; and an output unit which outputs the corrected concentration of the specific ground substance.

6. The monitoring apparatus according to claim 5, wherein the correction unit obtains a concentration x(t) of said specific ground substance based on the formula $$x(t)=(y(t)-y'(t))/(a-b)$$

wherein in the formula, the first signal value y(t) at a certain point of time t is expressed by a linear function $$y(t)=ax(t)+c,$$

where a is a calibration curve coefficient corresponding to the first biocatalyst, x is a concentration of the specific ground substance and c is a signal component based on a substance excluding the specific ground substance in a body fluid;

the second signal y'(t) at the certain point of time t is expressed by a linear function $$y'(t)=bx(t)+c,$$

where b is a calibration curve coefficient corresponding to the second biocatalyst, x is the concentration of the specific ground substance and c is the signal component; and a value of the signal component c in the first signal value y(t) is equal to a value of the signal component c of the second signal value y'(t).

* * * * *